(12) United States Patent
Ragan et al.

(10) Patent No.: US 6,262,272 B1
(45) Date of Patent: Jul. 17, 2001

(54) METHOD OF SYNTHESIS OF PYRROLE AMIDES

(75) Inventors: John Anthony Ragan, Gales Ferry; Teresa Woodall Makowski, Salem; David Jon Am Ende, Waterford; Pamela Jane Clifford, Preston; Gregory Randall Young, Gales Ferry; Alyson Kay Conrad, Ledyard; Shane Allen Eisenbeis, Pawcatuck; George Joseph Quallich, North Stonington; Douglas John Meldrum Allen, New London, all of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/403,985

(22) PCT Filed: Oct. 21, 1998

(86) PCT No.: PCT/IB98/01672

§ 371 Date: Jan. 19, 2000

§ 102(e) Date: Jan. 19, 2000

(87) PCT Pub. No.: WO99/25684

PCT Pub. Date: May 27, 1999

Related U.S. Application Data

(60) Provisional application No. 60/074,266, filed on Feb. 10, 1998, and provisional application No. 60/065,422, filed on Nov. 13, 1997.

(51) Int. Cl.$^7$ ............... C07D 401/00; C07D 209/42; C07D 307/78
(52) U.S. Cl. ............... 546/278.1; 548/492; 549/467
(58) Field of Search ............... 560/33; 548/492; 549/467; 546/278.1

(56) References Cited

FOREIGN PATENT DOCUMENTS

| 9511885 | 5/1995 | (WO) . |
| 9726243 | 7/1997 | (WO) . |
| 9734870 | 9/1997 | (WO) . |
| 9802420 | 1/1998 | (WO) . |
| 9802433 | 1/1998 | (WO) . |

OTHER PUBLICATIONS

Walter et al., CA 132:265083, 2000.*

* cited by examiner

Primary Examiner—Deborah C. Lambkin
(74) Attorney, Agent, or Firm—Peter C. Richardson; Paul H. Ginsburg; Seth A. Jacobs

(57) ABSTRACT

A method for preparing pyrrole-carboxyamides which selectively bind to GABAa receptors; which comprises reacting 1,3-cycloakane-diones with bromoethylacetate followed by reaction of the resulting product with an acid halide followed by reaction with an aromatic amine and finally with an amonium source at an elevated temperature.

12 Claims, No Drawings

METHOD OF SYNTHESIS OF PYRROLE AMIDES

Provisional Appln No. 60/065,422, Nov. 13, 1999. Provisional Appln No. 60/074,266, Feb. 10, 1998. This Appln is a 371 of PCT/IB98/01672, Oct. 12, 1998.

BACKGROUND OF THE INVENTION

1. Field of the Invention

This invention relates a method for synthesis of novel fused pyrrolecarboxamides which selectively bind to GABAa receptors. This invention also relates to chemical intermediates for synthesis of such compounds. Compounds which bind to GABAa receptors are useful in treating anxiety, sleep and seizure disorders, and overdoses of benzodiazepine-type drugs, and enhancing alertness.

2. Description of the Related Art

γ-Aminobutric acid (GABA) is regarded as one of the major inhibitory amino acid transmitters in the mammalian brain. Over 30 years have elapsed since its presence in the brain was demonstrated (Roberts & Frankel, J. Biol. Chem 187: 55–63, 1950; Udenfriend, J. Biol. Chem. 187:65–69, 1950). Since that time, an enormous amount of effort has been devoted to implicating GABA in the etiology of seizure disorders, sleep, anxiety and cognition (Tallman and Gallager, Ann. Rev. Neuroscience 8: 21–44, 1985). Widely, although unequally, distributed through the mammalian brain, GABA is said to be a transmitter at approximately 30% of the synapses in the brain. In most regions of the brain, GABA is associated with local inhibitory neurons and only in two regions is GABA associated with longer projections. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Recent investigations have indicated that the complex of proteins associated with postsynaptic GABA responses is a major site of action for a number of structurally unrelated compounds capable of modifying postsynaptic responses to GABA. Depending on the mode of interaction, these compounds are capable of producing a spectrum of activities (either sedative, anxiolytic, and anticonvulsant, or wakefulness, seizures, and anxiety).

1,4-Benzodiazepines continue to be among the most widely used drugs in the world. Principal among the benzodiazepines marketed are chlordiazepoxide, diazepam, flurazepam, and triazolam. These compounds are widely used as anxiolytics, sedative-hypnotics, muscle relaxants, and anticonvulsants. A number of these compounds are extremely potent drugs; such pofency indicates a site of action with a high affinity and specificty for individual receptors. Early electrophysiological studies indicated that a major action of benzodiazepines was enhancement of GABAergic inhibition. The benzodiazepines were capable of enhancing presynaptic inhibition of a monosynaptic ventral root reflex, a GABA-mediated event (schmidt et al., 1967, Arch. Exp. Path. Pharmakol. 258: 69–82). All subsequent electrophysiological studies (reviewed in Tallman et al. 1980, Science 207: 274–81, Haefley et al., 1981, Handb. Exptl. Pharmacol. 33: 95–102) have generally confirmed this finding, and by the mid-1970s, there was a general consensus among electrophysiologists that the benzodiazepines could enhance the actions of GABA.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior.

Studies on the mechanistic nature of these interactions depended on the demonstration of a high-affinity benzodiazepine binding site (receptor). Such a receptor is present in the CNS of all vertebrates phylogenetically newer than the boney fishes (Squires & Braestrup 1977, Nature 166: 732–34, Mohler & Okada, 1977, Science 198: 854–51, Mohler & Okada, 1977, Br. J. Psychiatry 133. 261–68). By using tritiated diazepam, and a variety of other compounds, it has been demonstrated that these benzodiazepine binding sites fulfill many of the criteria of pharmacological receptors; binding to these sites in in vitro is rapid, reversible, stereospecific, and saturable. More importantly, highly significant correlations have been shown between the ability of benzodiazepines to displace diazepam from its binding site and activity in a number of animal behavioral tests predictive of benzodiazepine potency (Braestrup & Squires 1978, Br. J. Psychiatry 133: 261–68). The average therapeutic doses of these drugs in man also correlate with receptor potency (Tallman et al. 1980, Science 207: 274–281.

Certain fused pyrrolecarboxamides which are useful as GABA brain receptor ligands are disclosed in U.S. Pat. No. 5,484,944 which is hereby incorporated by reference. These compounds may be prepared by the scheme shown below.

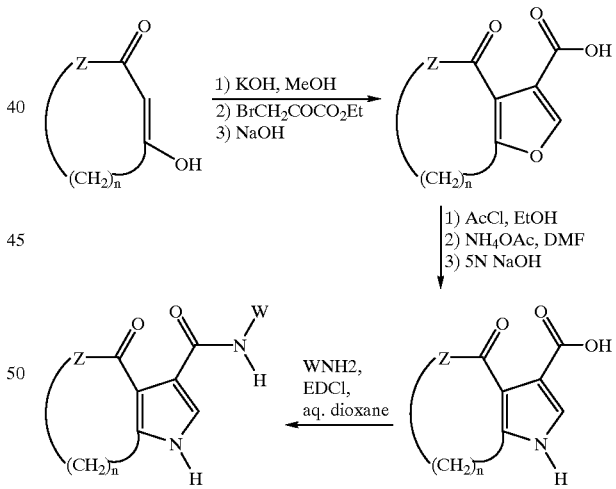

wherein z is N—R or a carbon atom substituted with R groups; and W is an optionally substituted aromatic ring.

SUMMARY OF THE INVENTION

This invention provides a method for preparing a compound of the formula

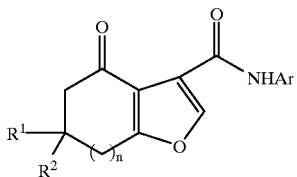

wherein $R^1$ and $R^2$ are independently selected from hydrogen and $C_1$–$C_6$ alkyl; and Ar is phenyl or heterocycle; or phenyl or heterocycle substituted with up to three substituents selected from $C_1$–$C_6$ alkoxy, $C_1$–$C_6$ alkyl, $C_2$–$C_6$ alkenyl, $C_1$–$C_6$ perflouroalkyl, $C_1$–$C_6$ alkoxy, $C_1$–$C_6$ perfluoroalkoxy, F, Cl, Br, —O—$(CH_2)_k$—O—, or $(CH_2)_m$ $NR^1R^2$; wherein n is an integer selected from 0 to 2;
m is an integer selected from 0 to 6; and
k is an integer selected from 1 or 2;
which comprises:
1) Reacting a compound of the formula

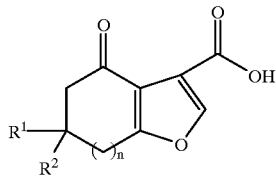

with an excess of an acid chloride or anhydride in a reaction inert solvent containing an excess of an acid acceptor until reaction is complete;
2) Adding an equivalent amount of $NH_2$—Ar to the solution of step 1 and holding until reaction is complete.

This invention also provides a method for preparing a compound of the formula

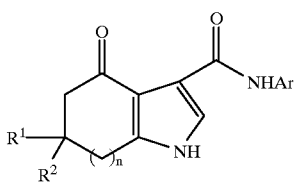

which comprises:
reacting a compound of formula II with an excess of an ammonium source in a reaction inert solvent at an elevated temperature until reaction is complete.

This invention also provides a method for preparing a compound of formula III wherein Ar is 2-fluoromethoxy phenyl, (4methyl-N-t-butylcarbamic ester)-amino methyl phenyl, 4-ethoxy phenyl or 4-methoxyphenyl, 4fluorophenyl, 4-pyridyl or 3-pyridyl, b-(2-hydroxyethoxy)-3-pyridyl, benzo[1,3] dioxol-5-yl. This invention also provides a method for preparing a compound of formula I wherein n is 2 and $R^1$ and $R^2$ are hydrogen; n is 1 and $R^1$ and $R^2$ are methyl; n is one and $R^1$ and $R^2$ are hydrogen; n is zero and $R^1$ and $R^2$ are hydrogen; and n is 1, $R^1$ is methyl and $R^2$ is hydrogen.

In another aspect this invention provides the compound of formula 1 which is 4-Oxo-5,6,7,8-tetrahydro-4H-cyclohepta[b]furan-3-carboxylic acid, 4-Oxo-5,6,7,8-tetrahydro-4H-cyclohepta[b]furan-3-carboxylic acid (2-fluoro-4-methoxyphenyl)-amide, 6,6-Dimethyl-4-oxo-4,5,6,7-tetrahydro-benofuran-3-carboxylic acid (2-fluoro-4-methoxyphenyl)-amide, 4-[(4-Oxo-4,5,6,7-tetrahydro-benzofuran-3-carbonyl)-amino]-benzylmethyl-carbamic acid tert-butyl ester, 4-[(4-Oxo-4,5,6,7-tetrahydro-1H-indole-3-carbonyl)-amino]-benzyl-methyl-carbamic acid tert-butyl ester, 4-Oxo-5,6-dihydro-4H-cyclopenta[b]furan-3-carboxylic acid (4-ethoxy-phenyl)-amide, 4-Oxo-5,6,7,8-tetrahydro-4H-cyclohepta[b]furan-3-carboxylic acid benzo[1,3]dioxol-5-ylamide, 4-Oxo-5,6,7,8-tetrahydro-4H-cyclohepta[b]furan-3-carboxyric acid-(4-methoxy-phenyl)-amide, 6-Methyl-4-oxo-4,5,6,7-tetrahydro-benzofuran-3-carboxylic acid (4-fluoro-phenyl)-amide, 6-Methyl-4-oxo-4,5,6,7-tetrahydro-benzofuran-3-carboxylic acid pyridin-4-ylamide, 6-Methyl-4-oxo-4,5,6,7-tetrahydro-benzofuran-3-carboxylic acid pyridin-3-ylamide, 6-Methyl-4-oxo-4,5,6,7-tetrahydro-berzofuran-3-carboxylic acid [6-(2-hydroxy-ethoxy)-pyridin-3-yl]-amide, and 4-Oxo-4,5,6,7-tetrahydro1H-indole-3carboxylic acid (4-methylaminomethyl-phenyl)-amide.

This invention also provides the intermediate compounds:

(4-Nitrobenzyl)-methyl-carbamic acid tert-butyl ester, and (4-Aminobenzyl)-methyl-carbamic acid tert-butyl ester.

This invention also provides a method of preparing a compound of Formula III
wherein:

Ar is substituted with —$(CH_2)_m$ NH $R^1$ which comprises: reacting a compound of the formula

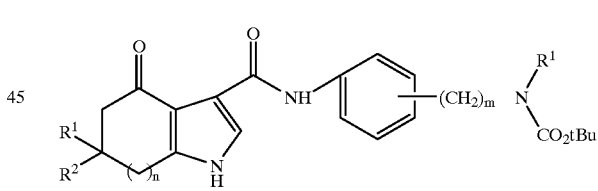

with water in the presence of acid.

DETAILED DESCRIPTION OF THE INVENTION

The method of this invention is illustrated by the scheme shown below.

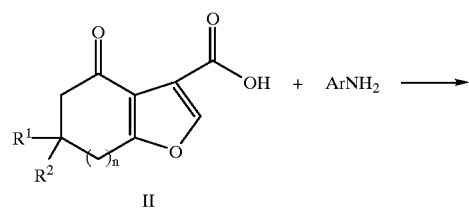

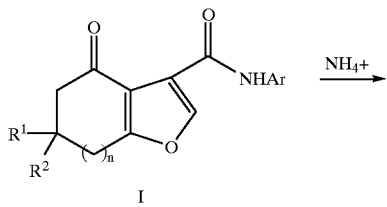

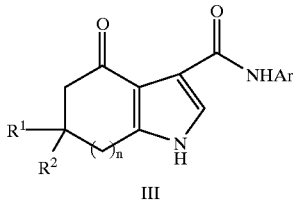

wherein Ar, $R^1$, $R^2$ and n are as defined above.

Compounds of formula II are readily prepared by reacting the appropriate 1,3-diketone with halo pyruvic acid ester, preferably ethylbromopyruvate as described in U.S. Pat. No. 5,484,944 and general procedure A of Example 1 of the present invention.

Compound I is prepared from compound II by converting the carboxylic acid group of compound I to the mixed acid anhydride and thence to the carboxanilide by reaction of the acid anhydride with the selected aniline in the presence of base. The reaction is preferably carried out in a reaction inert solvent at a reduced temperature without isolation of the intermediate acid anhydride.

Any acid chloride or anhydride may be used to form the mixed acid anhydride, ethylchloroformate is a preferred reagent.

The above-reaction is illustrated in general procedure B of Example 1 below.

Conversion of compound I to the final product (compound III) is accomplished by reaction of compound I with an ammonium salt in a reaction inert solvent at an elevated temperature adequate to insure reaction in a reasonable period of time. Any polar reaction inert solvent is suitable; n-methyl pyrrolidonone is preferred. Ammonium acetate is a convenient source of ammonium ion.

This procedure is illustrated in general procedure C of Example 1 below.

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

The invention is illustrated further by the following examples which are not to be construed as limiting the invention in scope or spirit to the specific procedures described in them.

EXAMPLE 1

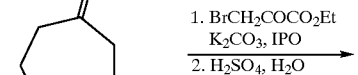

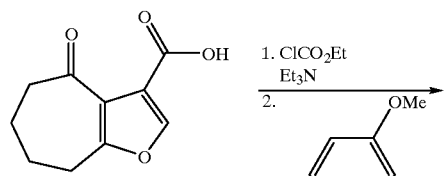

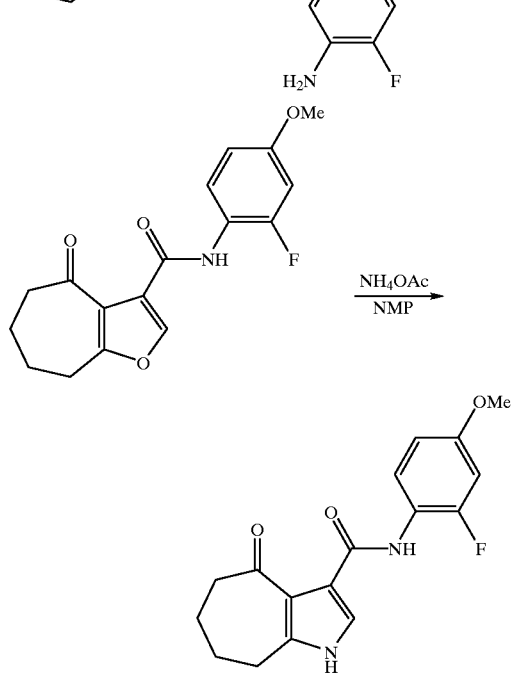

4-Oxo-5,6,7,8-tetrahydro-4H-cyclohepta[b]furan-3-carboxylic acid
General Procedure A (diketone to furan carboxlic acid):

Cycloheptane-1,3-dione (22.1 g, 174 mmol) was dissolved in 176 mL of isopropanol and cooled to 0° C. Ethyl bromopyruvate (21.9 mL, 174 mmol) was added, followed by $K_2CO_3$ (24.2 g, 175 mmol). The solution was then allowed to warm to room temperature and stirred for 16 hours. 220 mL of water were added, and the solution was extracted with four 110 mL portions of dichloromethane. The combined organic extracts were then washed with brine, and concentrated to provide an orange-brown oil. 220 mL of 1 N $H_2SO_4$ was then added, and the solution warmed in an 85° C. oil bath for 16 hours. After cooling to room temperature, the solution was extracted with two 220 mL portions of dichloromethane. The combined organic extracts were washed with brine, and concentrated to provide 37.2 g of a tan solid. This crude product was then granulated with 170 mL of methyl t-butyl ether, warming nearly to reflux for 30 min, followed by stirring at room temperature for 16 hours. Filtration provided the product as an off-white solid, 14.6 g (75 mmol, 43% yield from the diketone).

$^1$H nmr (CDCl$_3$): 8.07 (s, 1H), 3.14–3.10 (m, 2H), 2.89–2.86 (m, 2H), 2.05–1.93 (m, 4H).

MS (Cl): 195 (M+1, 100)

4-Oxo-5,6,7,8-tetrahydro4H-cyclohepta[b]furan-3-carboxylic acid (2-fluoro-4-methoxy-phenyl)-amide General Procedure B (furan carboxylic acid to furan carboxamide):

A solution of furan acid from Procedure A (7.65 g, 39.4 mmol) was dissolved in 80 mL dichloromethane and cooled to 0° C. Triethylamine (7.1 mL, 51 mmol) was added, followed by ethyl chloroformate (4.5 mL, 47 mmol). After 20 min, 2-fluoro-4-methoxyaniline (5.56 g, 39.4 mmol) was added in several small portions. The solution was allowed to warm to room temperature and stirred for 5 hours. The reaction mixture was worked up by diluting with dichloromethane, washing with brne, and drying over $MgSO_4$. Filtration and concentration provided 15.0 g of an off-white solid, which was granulated with 100 mL of methyl t-butyl ether for 16 hours. Filtration then provided 11.71 g of product (36.9 mmol, 94% yield) as a tan-white solid:

m.p. 168–172° C.

$^1$H nmr (CDCl$_3$): 8.28–8.24 (m, 1H), 8.10 (s, 1H), 6.72–6.66 (m, 2H), 3.78 (s, 3H), 3.11–3.06 (m, 2H), 2.86–2.83 (m, 2H), 2.01–1.93 (m, 4H)

MS (Cl): 318 (M+1, 100)

4-Oxo-1,4,5,6,7,8-hexahydro-cycloheptal[b]pyrrole-3-carboxylic acid (2-fluoro-4-methoxy-phenyl)-amide General Procedure C (furan carboxamide to pyrrole carboxamide):

A 500 mL flask was charged with 4-Oxo5,6,7,8-tetrahydro4H-cyclohepta[b]furan-3-carboxylic acid (2-fluoro-4-methoxy-phenyl)-amide from Procedure B (10.0 g, 31.5 mmol), ammonium acetate (12.1 g, 158 mmol), and 20 mL of N-methyopyrrolidinone. The resulting slurry was warmed in a 100° C. oil bath under a static atmosphere of nitrogen for 20 h. After cooling to room temperature, the reaction solution was treated with 180 mL water, added dropwise over a period of 30 min. The resulting solids were granulated for 6 h, then collected via filtration. After 16 h in a vacuum oven at 30° C., the product was isolated as a tan-brown solid (9.12 g, 28.8 mmol, 91% yield):

m.p. 158–159° C.

$^1$H nmr (CDCl$_3$): 12.62 (s, 1H), 11.25 (br s, 1H), 8.11–8.06 (m, 1H), 7.53 (br s 1H), 6.70–6.63 (m, 2H), 3.76 (s, 3H), 2.86–2.81 (m, 2H), 2.76–2.72 (m, 2H), 1.99–1.75 (m, 4H).

$^{13}$C nmr (d$_6$-DMSO): (14 of 17 lines observed) 201.1, 161.3, 147.3, 126.2, 120.9, 118.2, 115.3, 114.8, 107.9, 56.7, 41.5, 25.8, 23.5, 21.1

EXAMPLE 2

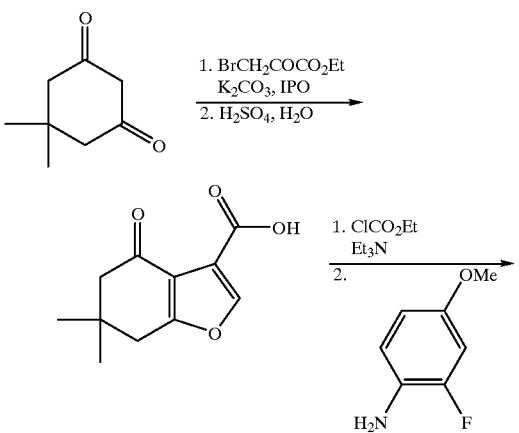

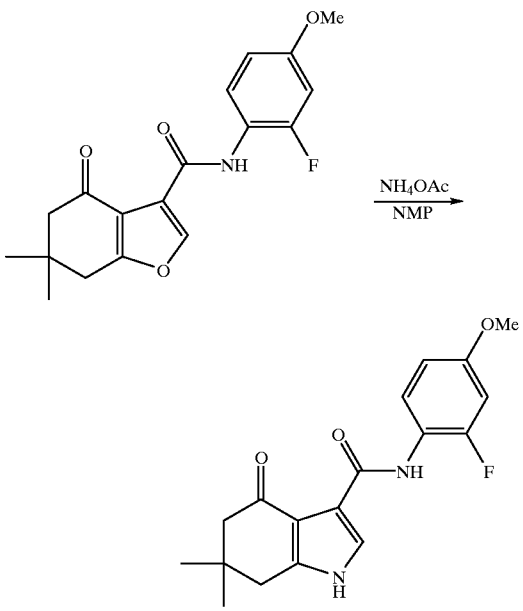

6,6-Dimethyl-4-oxo-4,5,6,7-tetrahydro-benzofuran-3-carboxylic acid (2-fluoro-4-methoxy-phenyl)-amide Starting with (6,6-dimethyl-4-oxo4,5,6,7-tetrahydro-benzofuran-3-carboxylic acid), prepared from dimedone by Procedure A, and 2-fluoro-4-methoxyaniline, General Procedure B provided the title compound as a white solid:

m.p. 174–176° C.

$^1$H nmr (CDCl$_3$): 8.23 (t, J=9, 1H), 8.09 (s, 1H), 6.64 (m, 2H), 3.75 (s, 3H), 2.79 (s, 2H), 2.50 (s, 2H), 1.15 (s, 6H)

MS (Cl): 332 (M+1, 100)

6,6-Dimethyl-4-oxo-4,5,6,7-tetrahydro-1H-indole-3-carboxylic acid (2-fluoro-4-methoxy-phenyl)-amide Starting with (6,6-dimethyl-4-oxo-4,5,6,7-tetrahydro-benzofuran-3-carboxylic acid (2-fluoro-4-methoxy-phenyl)-amide), General Procedure C provided the title compound as a white solid:

m.p. 203–205° C.

$^1$H nmr (CDCl$_3$): 12.40 (s, 1H), 11.45 (br s. 1H), 8.08 (t J=8.8 Hz, 1H), 7.49 (d, J=1.8 Hz, 1H), 6.72–6.64 (m, 2H), 3.77 (s, 3H), 2.55 (s, 2H), 2.42 (s, 2H), 1.04 (s, 6H).

$^{13}$C nmr (d$_6$-DMSO): (17 of 18 lines observed) 196.0, 161.3, 156.4, 154.0, 146.9, 127.4, 124.2, 120.3, 118.5, 114.1, 110.0, 102.1, 56.0, 52.0, 36.9, 35.5, 28.2.

EXAMPLE 3

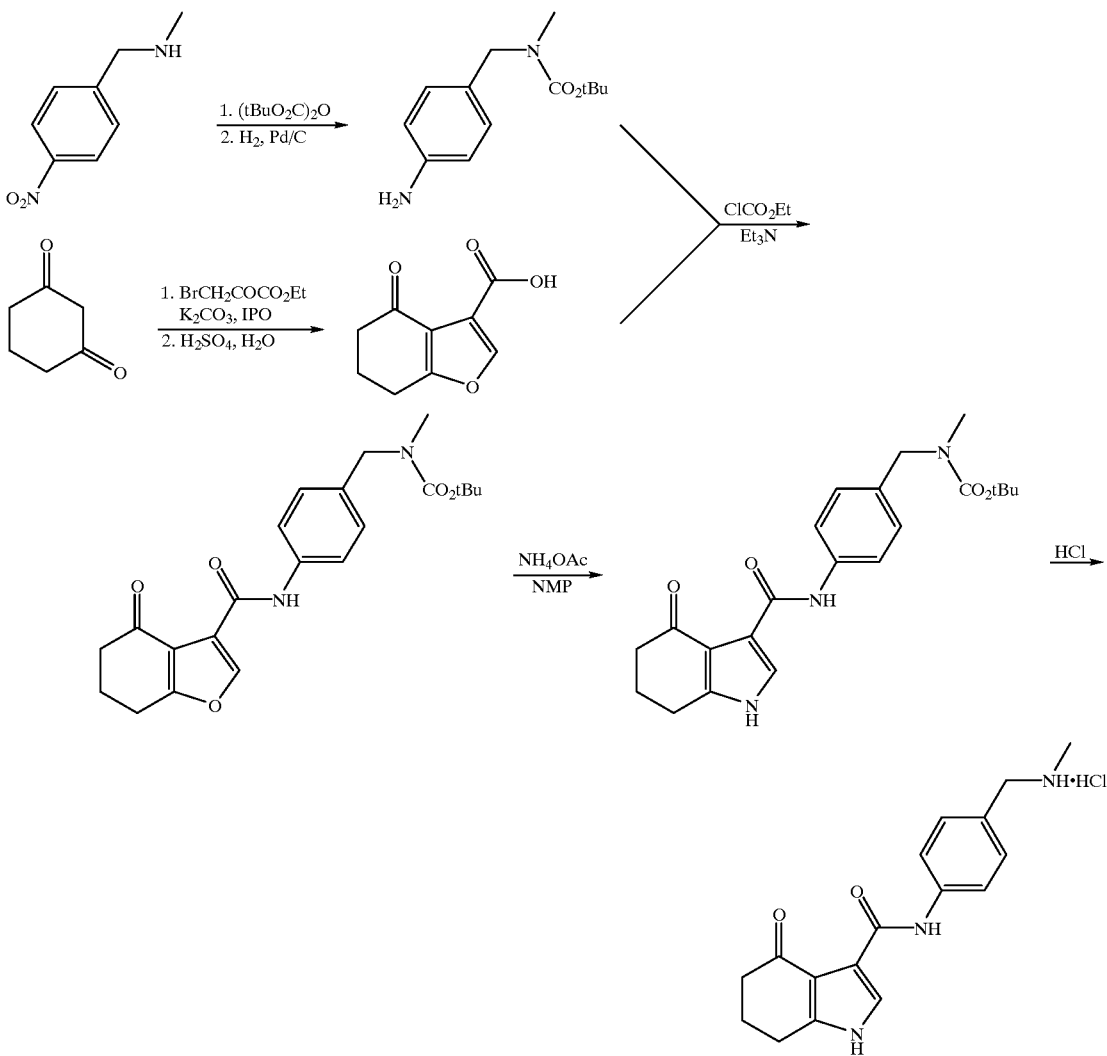

(4-Nitrobenzyl)-methylcarbamic acid tert-butyl ester

To a solution of $(tBuO_2C)_2O$ (24.9 g, 114 mmol) in 100 mL EtOAc was added dropwise a solution of (4-nitrobenzyl)-methylamine (19.0 g, 114 mmol) (*J. Chem. Soc.* 1925, 127, p. 1814) in 19 mL EtOAc. The resulting solution was stirred at room temperature or 60 min. then poured into 100 mL water. The organic phase was separated, dried over $MgSO_4$, filtered, and concentrated to provide the title compound as a pale yellow oil (30.0 g, 113 mmol, 99% yield):

$^1$H nmr ($CDCl_3$): (two amide bond rotamers) 8.17–8.15 (m, 2H), 7.35–7.33 (m, 2H), 4.48 (br s, 2H), 2.86–2.80 (overlapping br singlets, 3H), 1.46–1.40 (overlapping br singlets, 9H).

(4-Aminobenzyl)-methyl-carbamic acid tert-butyl ester

A Parr bottle was charged with (4-nitrobenzyl)-methycarbarnic acid tert-butyl ester (30.0 g, 113 mmol), 150 mL EtOAc, and 10% Pd/C (3.0 g, 10 wt %), and shaken under 40 psi hydrogen for 90 min. When hydrogen uptake ceased, the reaction vessel was purged with nitrogen, filtered through celite, and concentrated to provide a tan solid, which was granulated with 300 mL of isopropyl ether to provide the title compound as an off-white solid (17.7 g in two crops, 75 mmol, 66% yield):

$^1$H nmr ($CDCL_3$): (two amide bond rotamers) 6.99 (m, 2H), 6.67–6.59 (m, 2H), 4.26 (br s, 2H), 3.68 (br s, 2H), 2.75–2.71 (overlapping br singlets, 3H), 1.45–1.41 (overlapping br singlets, 9H).

4-[(4-Oxo-4,5,6,7-tetrahydro-benzofuran-3-carbonyl)-amino]-benzyl-methyl-carbamic acid tert-butyl ester Starting with (4,5,6,7-tetrahydro-benzofuran-3-carboxylic acide) and (4-aminobenzyl)-methyl-carbamic acid tert-butyl ester, General Procedure B provided the title compound as a white solid:

m.p. 150° C.

$^1$H nmr ($CDCl_3$): 8.06 (s, 1H), 7.71 (d, J=8, 2H), 4.35 (fr s, 2H), 2.92 (t, J=6, 2H), 2.78 (br s, 3H), 2.62 (t, J=6, 2H), 2.20 (m, 2H), 1.44 (s, 9H).

$^{13}$C nmr ($CDCl_3$) (16 of 18 lines obsrved): 197.5, 170.2, 159.1, 148.9, 137.7, 133.6, 127.8, 121.9, 119.9, 116.8, 79.0, 37.8, 33.7, 28.4, 23.5, 22.1

4-[(4-Oxo-4,5,6,7-tetrahydro-1H-indole-3-carbonyl)-amino]-benzyl-methyl-carbamic acid tert-butyl ester Following General Procedure C using (4-[(4-Oxo-4,5,6, 7-tetrahydro-benzofuran-3-carbonyl)-amino]-benzyl-methyl-carbamic acid tert-butyl ester) provided the title compound as a pale yellow oil:

¹H nmr (CDCl₃): 7.76 (d, J=8, 2H), 7.47 (s, 1H), 7.17 (d, J=8, 2H), 4.36 (br s, 2H), 2.77 (t, J=6, 2H), 2.76 (br s, 3H), 2.55 (t, J=6, 2H), 2.08 (t, J=6, 2H), 1.44 (br s, 9H)

¹³C nmr (CDCl₃) (17 of 18 lines observed): 196.9, 162.5, 148.0, 138.2, 133.3, 128.2, 127.9, 126.2, 120.3, 119.6, 115.6, 79.8, 38.2, 33.8, 28.4, 23.4, 22.8

MS (Cl): 396 (M-1, 100)

4-Oxo-4,5,6,7-tetrahydro-1H-indole-3-catboxylic acid (4-methylaminomethyl-phenyl)-amide A solution of 4-[(4-Oxo-4,5,6,7-tetrahydro1H-indole-3-carbonyl)-amino]-benzyl-methyl-carbamic acid tert-butyl ester (5.0 g, 13 mmol) in 50 mL of 95% EtOH was treated with 15 mL of concentrated HCl. After 24 hours, the slurry was cooled to 0° C., and the solids collected by filtration to provide the title compound as its HCl salt, 3.21 g (9.6 mmol, 74% yield) as a white solid:

¹H nmr (CD₃OD): 12.88 (br s, 1H), 7.82 (d, J=8.5 Hz, 2H), 7.49 (d, J=8.5 Hz, 2H), 4.15 (s, 2H), 2.91–2.88 (m, 2H), 2.71 (s, 3H), 2.6–2.61 (m, 2H), 2.20–2.15 (m, 2H).

EXAMPLE 4

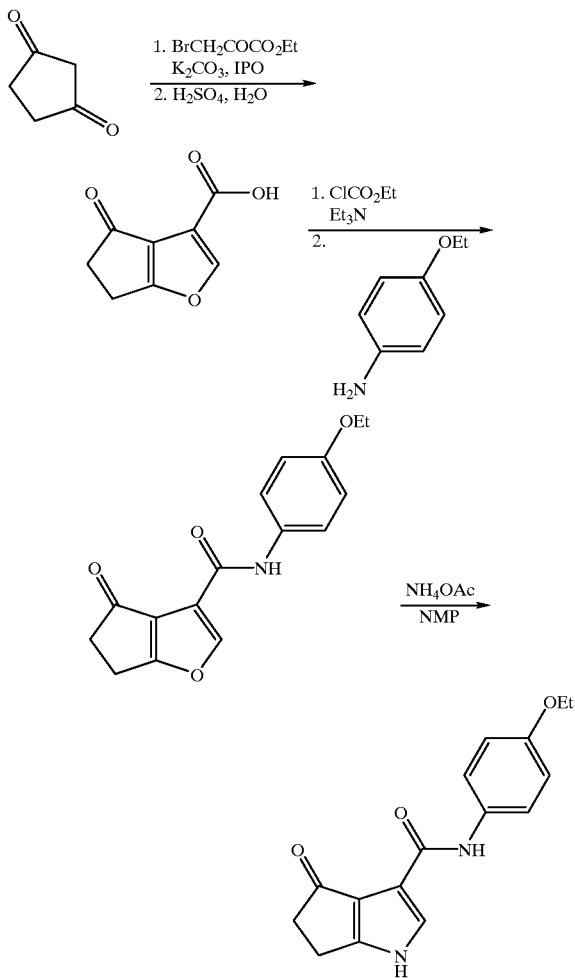

4-Oxo-5,6-dihydro-4H-cyclopenta[b]furan-3-carboxylic acid (4-ethoxy-phenyl)-amide Starting from 4-oxo-5,6-dihydro-4H cylopenta[b]furan-3-carboxylic acid and 4-ethoxyaniline, General Procedure B provided the title compound:

¹H nmr (CDCl₃): 9.68 (s, 1H), 8.15 (s, 1H), 7.65 (d, 2H); 6.88 (d, 2H), 4.02 (q, 2H), 3.14 (m, 4H), 1.4 (t, 3H)

4-Oxo-1,4,5,6-tetrahydro-cyclopenta[b]pyrrole-3-carboxylic acid (4-ethoxy-phenyl)-amide Starting from 4-oxo5,6-dihydro4H-cyclopenta[b]furan-3-carboxylic acid (4-ethoxy-phenyl)-amide, General Procedure C provided the title compound:

m.p. 273–275° C.

¹H nmr (DMSO-d₆): 12.14 (s, 1H), 10.37 (s, 1H), 7.58 (s, 1H), 7.54 (d, 2H), 6.90 (d, 2H), 3.95 (q, 2H), 2.95 (s, 4H), 1.29 (t, 3H)

EXAMPLE 5

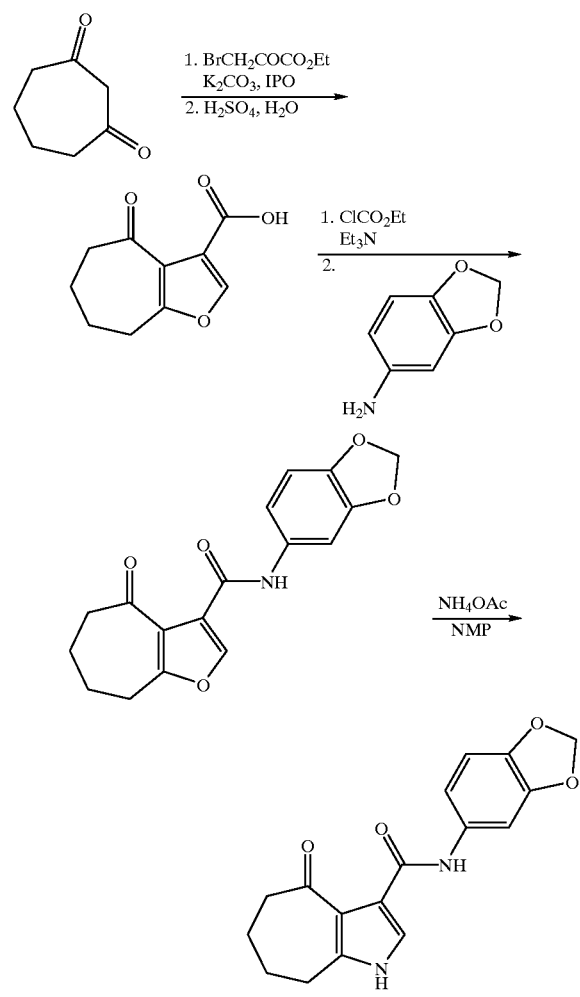

4-Oxo-5,6,7,8-tetrahydro4H-cyclohepta[b]furan-3-carboxylic acid benzo[1,3]dioxol-5-ylamide Starting from 4-oxo-5,6,7,8-tetrahydro4H-cyohepta[b]furan-3-carboxylic acid and benzo[1,3]dioxol-5-yiamine, General Procedure B provided the title compound:

¹H nmr (CDCl₃): 11.79 (s, 1H), 8.09 (s, 1H), 7.48 (s, 1H), 7.06 (d, 1H), 6.77 (d, 1H), 5.94 (s, 2H), 3.06 (t, 2H), 2.82 (t, 2H), 1.98 (br s, 4H)

4-Oxo-1,4,5,6,7,8hexahydro-cyclohepta[b]pyrrole-3-carboxylic acid benzo[1,3]dioxol-5-ylamide:

Starting from 4-oxo-5,6,7,8-tetrahydro-4H-cyclohepta[b]furan-3-carboxylic acid benzo[1,3]dioxol-5yiamide, General Procedure C provided the title compound:

m.p. 210–212° C.

¹H nmr (DMSO-d₆): 12.51 (s, 1H), 12.02 (s, 1H), 7.48 (s, 1H), 7.46 (s, 1H), 6.95 (d, 1H), 6.86 (d, 1H), 5.98 (s, 2H), 2.97 (br s, 2H), 2.74 (br s, 2H), 1.78 (br s, 4H)

EXAMPLE 6

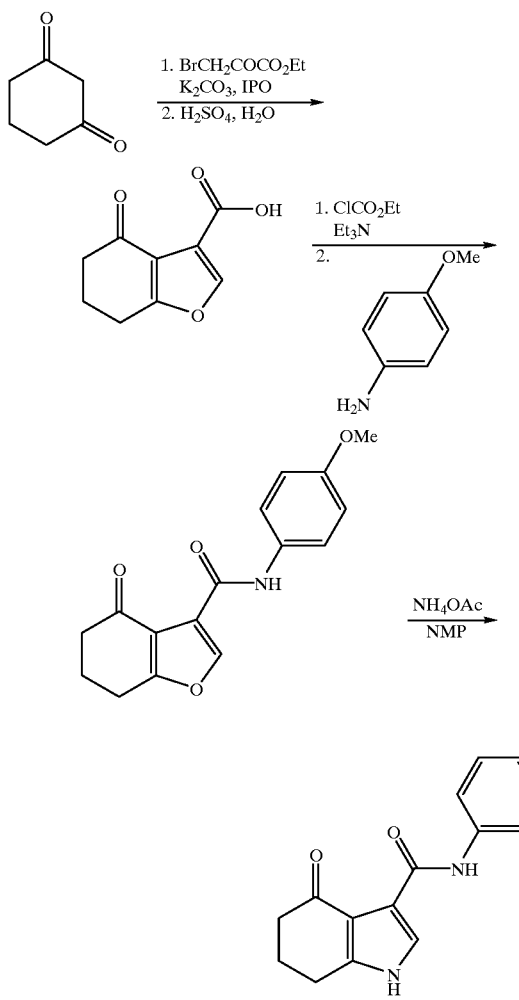

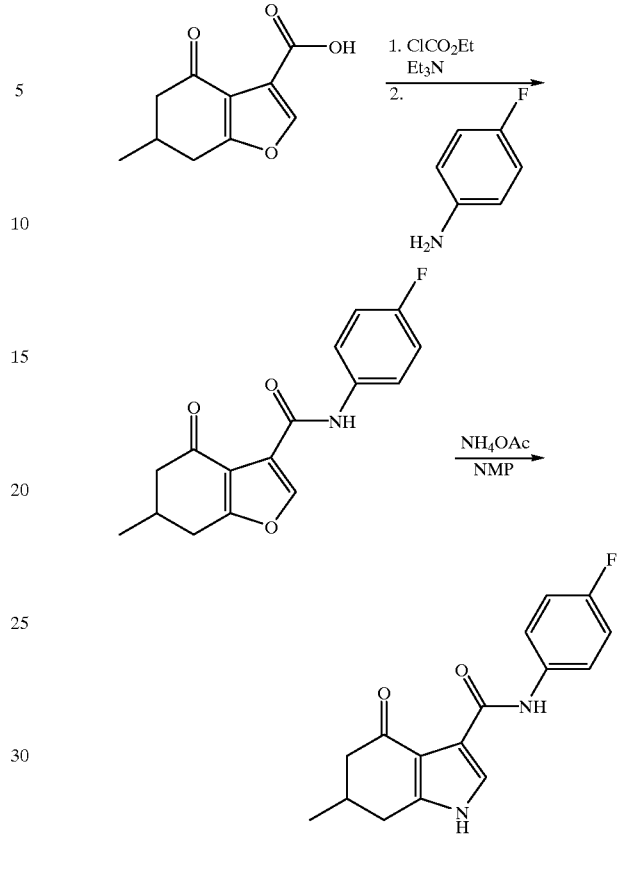

4-Oxo-5,6,7,8-tetrahydro-4H-cyclohepta[b]furan-3-carboxylic acid-(4-methoxy-phenyl)-amide Starting from 4-oxo-5,6,7,8-tetrahydro-4H-cylohepta[b]furan-3-carboxylic acid and 4-methoxyaniline, General Procedure B provided the title compound:

$^1$H nmr (CDCl$_3$): 11.75 (s, 1H), 8.10 (s, 1H), 7.67 (d, 2H), 6.86 (d, 2H), 3.80 (s, 3H), 3.08 (t, 2H), 2.82 (t, 2H), 1.98 (br s, 4H)

4-Oxo-1,4,5,6,7,8-hexahydro-cyclohepta[b]pyrrole-3-carboxylic acid (4-methoxy-phenyl)-amide:

Starting from 4-oxo-5,6,7,8-tetrahydro-4H-cyclohepta[b]furan-3-carboxylic acid-(4-methoxy-phenyl)-amide, General Procedure C provided the title compound:

m.p. 183–185° C.

$^1$H nmr (DMSO-d$_6$): 12.42 (s, 1H),12.02 (s, 1H), 7.60 (d, 2H), 7.48 (s,1H), 6.90 (d, 2H), 3.72 (s, 3H), 2.95 (br s, 2H), 2.73 (br s, 2H), 1.78 (br s, 4H)

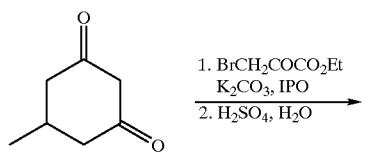

6-Methyl-4-oxo-4,5,6,7-tetrahydro-benzofuran-3-carboxylic acid:

Starting with 5methylcyclohexane-1,3-dione, General Procedure A provided the title compound:

MS (Cl): 193 (M-1, 100)

$^1$H nmr (CDCl$_3$): 13.17 (br singlet, 1H), 8.00 (s, 1H), 3.04 (ddd, J=0.8, 4.4, 17.2, 1H), 2.71–2.59 (m, 2H), 2.57–2.48 (m, 1H), 2.39 (ddd, J=0.8, 11.2, 16.8, 1H), 1.20 (d, J=6.4, 3H).

6-Methyl-4-oxo-4,5,6,7-tetrahydro-benzofuran-3-carboxylic acid (4-fluoro-phenyl)-amide:

Starting from 6-methyl-4-oxo-4,5,6,7-tetrahydro-benzofuran-3-carboxylic acid and 4-fluoroaniline, General Procedure B provided the title compound:

$^1$H nmr (CDCl$_3$): 11.71 (s, 1H), 8.09 (s, 1H), 7.73 (dd, 2H), 7.01 (t, 2H), 3.03 (dd, 1H), 2.72–2.59 (m, 2H), 2.54 (m, 1H), 2.39 (m, 1H), 1.21 (d, 3H)

6-Methyl-4-oxo-4,5,6,7-tetrahydro-1H-indole-3-carboxylic acid (4-fluoro-phenyl)-amide:

Starting from 6-methyl-4-oxo-4,5,6,7-tetrahydro-benzofuran-3-carboxylic acid (4-fluoro-phenyl)amide, General Procedure C provided the title compound:

m.p. 262–264° C.

$^1$H nmr (DMSO-d$_6$): 12.53 (s, 1H), 12.12 (s, 1H), 7.72 (dd, 2H), 7.54 (s, 1H), 7.18 (t, 2H), 2.92 (dd, 1H), 2.56 (m, 2H), 2.38 (m, 2H), 1.05 (d, 3H)

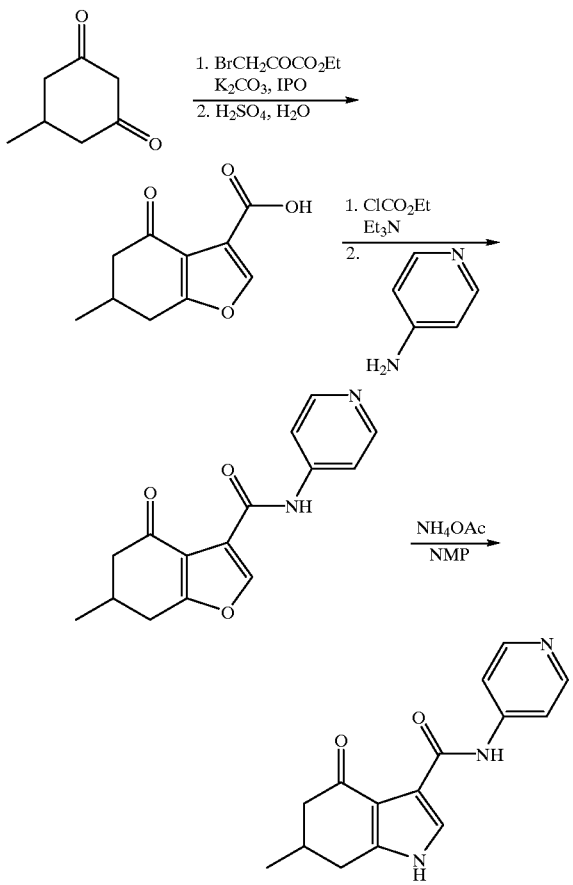

6-Methyl-4-oxo-4,5,6,7-tetrahydro-benzofuran-3-carboxylic acid pyridin-4-ylamide:

Starting from 6-methyl-4-oxo-4,5,6,7-tetrahydro-benzofuran-3-carboxylic acid and 4-aminopyridine, General Procedure B provided the title compound:

$^1$H nmr (CDCl$_3$): 12.14 (s, 1H), 8.53 (d, 2H), 8.15 (s, 1H), 7.78 (d, 2H), 3.06 (dd, 1H), 2.77–2.61 (m, 2H), 2.56 (m, 1H), 2.38 (m, 1H), 1.20 (d, 3H)

6-Methyl-4-oxo-4,5,6,7-tetrahydro-1H-indole-3-carboxylic acid pyridin-4-ylamide:

Starting from 6-methyl-4-oxo-4,5,6,7-tetrahydro-benzofuran-3-carboxylic acid pyridin-4-ylamide, General Procedure C provided the title compound:

m.p. 280–290° C. (dec.)

$^1$H nmr (DMSO-d$_6$): 12.81 (s, 1H), 12.21 (s, 1H), 8.42 (d, 2H), 7.65 (s, 1H), 7.53 (d, 2H), 2.92 (dd, 1H), 2.55 (m, 2H), 2.38 (m, 2H), 1.07 (d, 3H)

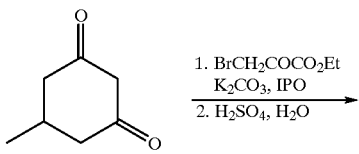

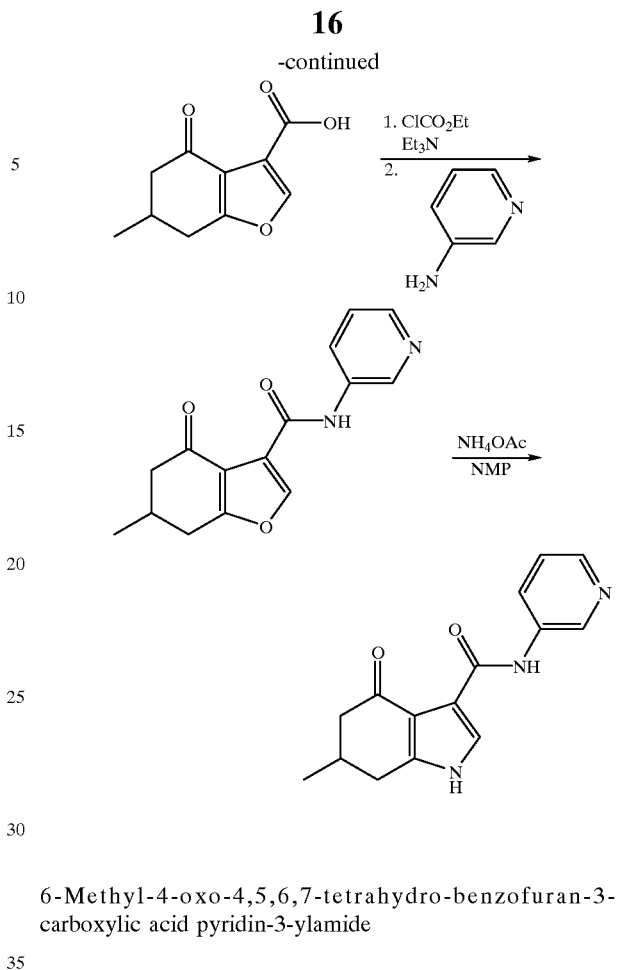

6-Methyl-4-oxo-4,5,6,7-tetrahydro-benzofuran-3-carboxylic acid pyridin-3-ylamide Starting from 6-methyl-4-oxo-4,5,6,7-tetrahydro-benzofuran-3-carboxylic acid and 3-aminopyridine, General Procedure B provided the title compound:

$^1$H nmr (CDCl$_3$): 11.90 (s, 1H), 8.90 (s, 1H), 8.38 (d, 1H), 8.31 (d, 1H), 8.13 (s, 1H), 7.28 (m, 1H), 3.06 (dd, 1H), 2.75–2.60 (m, 2H), 2.55 (m, 1H), 2.41 (m, 1H), 1.22 (d, 3H)

6-Methyl-4-oxo-4,5,6,7-tetrahydro-1H-indole-3-carboxylic acid pyridin-3-ylamide

Starting from 6-methyl-4-oxo-4,5,6,7-tetrahydro-benzofuran-3-carboxylic acid pyridin-3-ylamide, General Procedure C provided the title compound:

m.p. 225–227° C.

$^1$H nmr (DMSO-d$_6$): 12.67 (s, 1H), 12.17 (s, 1H), 8.81 (s, 1H), 8.24 (br s, 1H), 8.13 (d, 1H), 7.58 (s, 1H), 7.37 (m, 1H), 2.88 (dd, 1H), 2.54 (m, 2H), 2.39 (m, 2H), 1.05 (d, 3H)

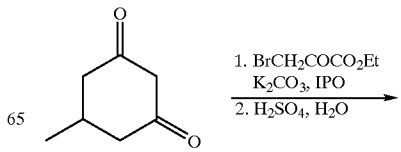

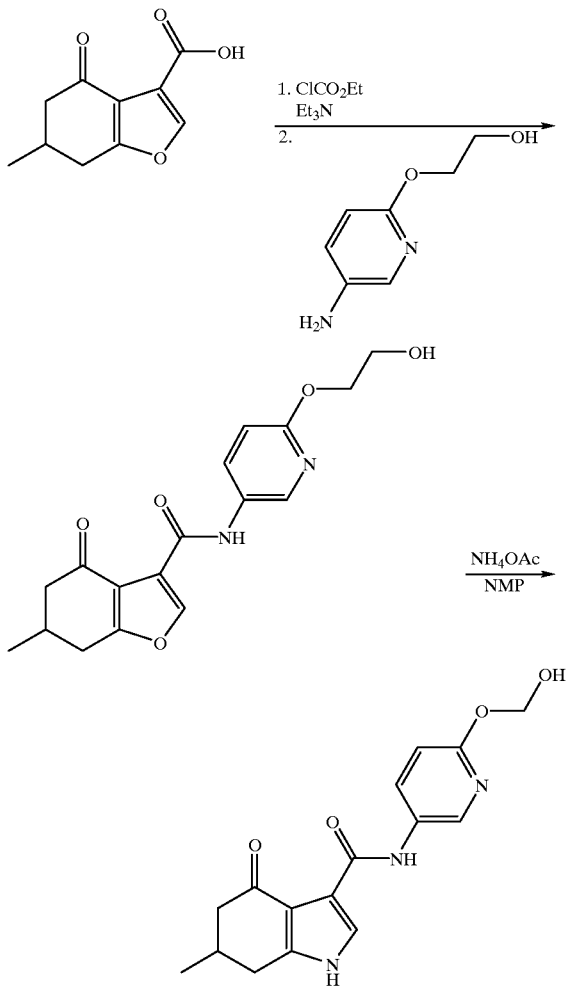

6-Methyl-4-oxo-4,5,6,7-tetrahydro-benzofuran-carboxylic acid [6-(2-hydroxy-ethoxy)-pyridin-3-yl]-amide Starting from 6-methyl-4-oxo-4,5,6,7-tetrahydro-benzofuran-3-carboxyiic acid and 3-amino-6-(2-hydroxyethoxy)-pyridine, General Procedure B provided the title compound:

$^1$H nmr (CDCl$_3$): 11.72 (s, 1H), 8.48 (s, 1H), 8.12 (d, 1H), 8.11 (s,1H), 6.79 (d, 1H), 4.42 (t, 2H), 3.97 (t, 2H), 3.62 (br s, 1H), 3.06 (dd, 1H), 2.73–2.60 (m, 2H), 2.53 (m, 1H), 2.39 (m, 1H), 1.05 (d, 3H)

6-Methyl-4-oxo-4,5,6,7-tetrahydro-1H-indole-3-carboxylic acid [6-(2-hydroxy-ethoxy)-pyridin-3-yl]-amide Starting from 6-methyl-4-oxo-4,5,6,7-tetrahydro-benzofuran-3-carboxylic acid [6-(2-hydroxy-ethoxy)-pyridin-3-yl]-amide, General Procedure C provided the title compound:

m.p. 183–185° C.

$^1$H nmr (DMSO-d$_6$): 12.42 (s, 1H), 12.11 (s,1H), 8.41 (s, 1H), 7.98 (d, 1H), 7.53 (s, 1H), 6.81 (d, 1H), 4.21 (t, 2H), 3.68 (t, 2H), 2.90 (dd, 1H), 2.55 (m, 2H), 2.38 (m, 2H), 1.05 (d, 3H)

PREPARATION I

Preparation of cycloheptane-1,3-dione:

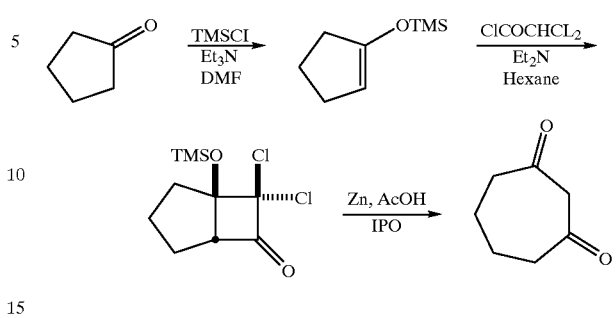

1-(Trimethylsiloxy)-cyclopentene:

A 1 L round bottom flask was charged with cyclopentanone (50.7 g, 0.603 mol) and DMF (250 mL). Triethylamine was added (200 mL, 1.45 mol), followed by dropwise addition of TMSCI (91 mL, 0.72 mol) over 5 min. The solution was then warmed to reflux (90° C.) for 26 h. After cooling to ambient temperature, the mixture was transferred to a separatory funnel, rinsing with 500 mL of hexanes. The solution was washed with water (3 portions of 100 mL each), brine (100 mL), then concentrated to give 110 g of a dark orange oil. $^1$H nmr analysis showed the desired product, plus 10–15% of triethylamine. This material was used in the next reaction without further purification.

7,7-Dichloro-1-(trimethylsiloxy)-bicyclo[32.0]heptan-6-one:

The crude TMS enol ether (2) (0.60 mol) was dissolved in 950 mL of hexanes in a 2 L round bottom flask. Triethylamine (100 mL, 0.72 mol) was added, followed by dichloroacetyl chloride (58 mL, 0.60 mol) as a solution in 450 mL hexanes, dropwise over 2 h. The solution was then stirred at ambient temperature overnight. The reaction mixture was then filtered through fritted glass, rinsing with several 50 mL portions of hexane. The clear solution was concentrated in vacuo to provide 128 g (80% over 2 steps) of product as a dark brown oil. This material was homogeneous by GC/MS and $^1$H nmr, save traces of Et$_3$N and DMF, and was used directly in the next reaction.

Cycloheptane-1,3-dione (1):

Dichlorocyclobutanone 3 (128 g, 0.48 mol) was dissolved in 520 mL of 1:1 isopropanol-water in a 2 L, 3-neck flask with an overhead stirrer. Zinc granules (126 g, 1.9 mol, −30+100 mesh) were added in one portion. After 60 min at room temperature, 130 mL of AcOH plus 260 mL of water were added dropwise via addition funnel (ca. 4 mL are added initially, followed by a 10 min hold to check for exotherms; 20 ml were then added, followed by another 10 min hold; once any exotherm has abated, the remaining acid solution was added dropwise; the entire addition takes 1.5–2 h). After 16 h, the mixture was transferred to a separatory funnel, decanting away from most of the zinc (several small isopropanol rinses were used). The isopropanol-AcOH-water mixture was then extracted with 5 portions of toluene (250 mL each), which are combined and concentrated to provide 51.7 g of product as a dark, orange-brown oil (85% crude mass balance, ca. 85% pure by $^1$H nmr). This material is suitable for subsequent reactions, or can be purified by distillation, which provided 29.4 g (0.23 mol, 49% yield) of product as a clear, colorless oil (b.p. 65–75° C. at 1.2 mm). It's spectral properties ($^1$H nmr, GC/MS) were identical to samples prepared by the oxymercurafion route of Chandrasekaran (*Synthetic Communications* 1984, 14, 339–345).

PREPARATION II
Preparation of 2-fluoro-4-methoxyaniline:

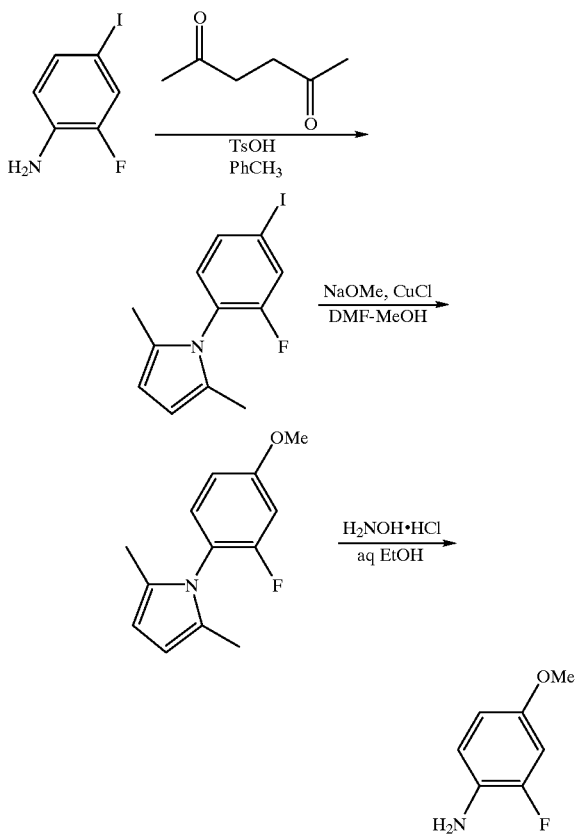

1-(2-Fluoro-4-iodo-phenyl)-2,5-dimethyl-1H-pyrrole:

A 500 mL round bottom flask was charged with 2-fluoro-4-iodoaniline (53.3 g, 220 mmol), toluene (250 mL), TsOH·H$_2$O (0.43 g, 2.3 mmol, 1 mol %), and acetonylacetone (30.8 g, 270 mmol, 1.2 eq). The solution was warmed to reflux under Dean-Stark conditions for 1 h, at which point GC/MS and TLC analysis indicate complete conversion to the pyrrole. The solution is cooled to room temperature, washed with aqueous NaHCO$_3$, dried over MgSO$_4$, filtered, and concentrated to provide a dark brown oil which crystallized upon standing (crude yield=72.8 g, 103% of theory). This material was homogeneous by HPLC and $^1$H nmr, and was suitable for use in the next reaction. An analytical sample was prepared by dissolving in 210 mL of hot hexanes, cooling, then concentrating to 50% of the original volume. Cooling in an ice bath with rapid stirring provided 35.5 g (49% recovery) of a brown, granular solid (m.p. 68–70° C.). $^1$H NMR (CDCl$_3$): d 7.43 (t, J=27 Hz, 2H), 7.13 (t, J=20 Hz, 1H), 5.94 (s, 2H), 2.02 (s, 6H); $^{13}$C NMR (CDCl$_3$) d 158.3 (d, J=254 Hz), 131.6, 128.9, 127.8 (d, J=3 Hz), 122.0, 120.3 (d, J=23 Hz), 106.4, 12.4; MS (EI): m/z 268 (100).

1-(2-Fluoro-4-methoxyphenyl)-2,5-dimethyl-1H-pyrrole:

The crude product from the previous reaction (1-(2-fluoro-4-iodo-phenyl)-2,5-dimethyl-1 H-pyrrole, 70.0 g, 222 mmol) was dissolved in 230 mL of MeOH and 70 mL of DMF. To this solution was added NaOMe (35.9 g, 666 mmol, 3.0 eq) and CuCl (3.3 g, 31 mmol, 15 mol %). The resulting mixture was warmed to reflux for 4 h. After cooling to room temperature, isopropyl ether (IPE) (500 mL), 5% aqueous NH$_4$Cl (220 mL), and water (350 mL) were added, and the mixture was stirred overnight. The mixture was then filtered through celite, the layers were separated, and the aqueous layer extracted with 350 mL of IPE. The combined organic extracts were then washed with 10% aqueous NH$_4$OH (200 mL), and passed through a pad of silica gel (100 g). Concentration provided a brown oil, which crystallized upon standing (45.2 g, 93% yield). Recrystallization from 135 mL of hot hexane provided 30.1 g (62% yield) of product as a brown solid, m.p. 67–69° C. $^1$H NMR (CDCl$_3$): d 7.12 (t, J=8 Hz, 1H), 6.75 (d, J=8 Hz, 1H), 6.73 (s, 1H), 5.89 (s, 2H), 3.82 (s, 3H), 1.97 (s, 6H); $^{13}$C NMR (CDCl$_3$) (9 of 10 lines observed) d 159.1 (d, J=260 Hz), 130.7, 129.5, 109.9 (d, J=3 Hz), 106.0, 105.6, 102.3 (d, J=25 Hz), 55.7, 12.4; MS (EI): m/z 219 (100).

2-Fluoro-4-methoxyaniline:

A 2 L round bottom flask is charged with 1-(2-fluoro-4-methoxy-phenyl)-2,5-dimethyl-1H-pyrrole (60.0 g, 271 mmol), H$_2$NOH·HCl (188 g, 2.71 mol, 10 eq), EtOH (600 mL), water (300 mL), and Et$_3$N (76 mL, 0.54 mol), then warmed to reflux for 16 h. After cooling to room temperature, the reaction mixture is slowly poured into 1.7 L of ice-cold 1 N HCl, and washed with two 500 mL portions of IPE. The aqueous phase was then brought to pH 10 by careful addition of 6 N NaOH, and extracted with two 500 mL portions of IPE. The organic extracts were concentrated to provide an oily solid, which was filtered, rinsing with additional IPE (the solid was not related to the aniline product by $^1$H nmr analysis, and is presumably some acetonylacetone related by-product of the deprotection). Further concentration of the IPE solution provided a brown oil (36 g, 98% yield), which was recrystallized from 200 mL of hot IPE, to provide 26.8 g (70% yield) of 2-fluoro-4-methoxyaniline 1 as a brown solid, m.p. 46–47° C. (lit 47–48° C.). Spectral data ($^1$H nmr, mass spec) were identical to samples prepared by the literature method (*Aust. J. Chem.* 1972, 25, 2621–2629).

What is claimed is:

1. A method for preparing a compound of the formula

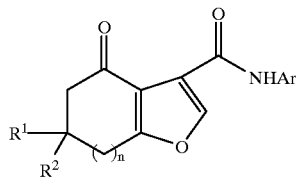

wherein R$^1$ and R$^2$ are independently selected from hydrogen and C$_1$–C$_6$ alkyl; and Ar is phenyl or heterocycle; or phenyl or heterocycle substituted with up to three substituents selected from C$_1$–C$_6$ alkoxy, C$_1$–C$_6$ alkyl, C$_2$–C$_6$ alkenyl, C$_1$–C$_6$ perflouroalkyl, C$_1$–C$_6$ alkoxy, C$_1$–C$_6$ perfluoroalkoxy, F, Cl, Br, —O—(CH$_2$)$_k$—O—, or (CH$_2$)$_m$NR$^1$R$^2$; or Ar is 4-(N-methyl-N-t-butylcarboxyaminomethyl)-phenyl wherein n is an integer selected from 0 to 2;

m is an integer selected from 0 to 6; and k is an integer selected from 1 or 2;

which comprises:
1) reacting a compound of the formula

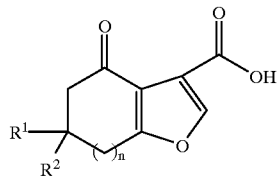

with an excess of an acid chloride or anhydride in a reaction inert solvent containing an excess of an acid acceptor until reaction is complete;
2) adding an equivalent amount of $NH_2$—Ar to the solution of step 1 and holding until reaction is complete.

2. A method according to claim 1 further comprising reacting a compound of formula I with an excess of ammonium source in a reaction inert solvent at an elevated temperature until reaction is complete to prepare a compound of the formula

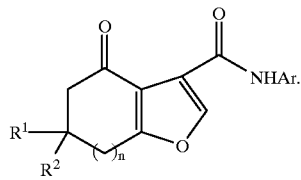

3. The iethod of claim 2 wherein Ar is selected from the group consisting of:
2-fluoro-4-methoxy phenyl,
4-(N-methyl-N-t-butylcarboxy-aminomethyl)-phenyl,
4-ethoxy phenyl,
4-methoxyphenyl,
4-fluorophenyl,
4-pyridyl or 3-pyridyl,
6-(2-hydroxyethoxy)-3-pyridyl, and benzo[1,3] dioxol-5-yl.

4. The method of claim 1 wherein n is 2 and $R^3$ and $l^2$ are hydrogen.

5. The method of claim 1 wherein n is 1 and $R^1$ and $R^2$ are methyl.

6. The method of claim 1 wherein n is one and $R^1$ and $R^2$ are hydrogen.

7. The method of claim 1 wherein n is zero and $R^1$ and $R^2$ are hydrogen.

8. The method of claim 1 wherein n is 1, $R^1$ is methyl and $R^2$ is hydrogen.

9. A compound selected from the group consisting of:
4-Oxo-5,6,7,8-tetrahydro-4H-cyclohepta[b]furan-3-carboxylic acid,
4-Oxo-5,6,7,8-tetrahydro-4H-cyclohepta[b]furan-3-carboxylic acid (2-fluoro-4-methoxy-phenyl)-amide,
6,6-Dimethyl-4-oxo-4,5,6,7-tetrahydro-benzofuran-3-carboxylic acid (2-fluoro-4-methoxy-phenyl)-amide,
4-[(4-Oxo-4,5,6,7-tetrahydro-benzofuran-3-carbonyl)-amino]-benzyl-methyl-carbamic acid tert-butyl ester,
4-Oxo-5,6-dihydro-4H-cyclopenta[b]furan-3-carboxylic acid (4-ethoxy-phenyl)-amide,
4-Oxo-5,6,7,8-tetrahydro-4H-cyclohepta[b]furan-3-carboxylic acid benzo[1,3]dioxol-5-ylamide,
4-Oxo-5,6,7,8-tetrahydro-4H-cyclobepta[b]furan-3-carboxylic acid-(4-methoxy-phenyl)-amide,
6-Methyl-4-oxo-4,5,6,7-tetrahydro-benzofuran-3-carboxylic acid (4-fluoro-phenyl)-amide,
6-Methyl-4-oxo-4,5,6,7-tetrahydro-benzofuran-3-carboxylic acid pyridin-4-ylamide
6-Methyl-4-oxo-4,5,6,7-tetrahydro-benzofuran-3-carboxylic acid pyridin-3-ylamide, and
6-Methyl-4-oxo-4,5,6,7-tetrahydro-benzofuran-3-carboxylic acid [6-(2-hydroxy-ethoxy)-pyridin-3-yl]-amide.

10. A compound which is 4-[(4-Oxo-4,5,6,7-tetrahydro-1H-indole-3-carbonyl)-amino]-benzyl-methyl-carbamic acid tert-butyl ester.

11. A method according to claim 2 wherein Ar is 4-(-methyl-N-t-butylcarboxy-aminomethyl)-phenyl which further comprises reacting the product of said method with water in the presence of acid.

12. A method of claim 2 wherein said acid chloride is ethylchloroformate.

* * * * *